United States Patent [19]

Venturello et al.

[11] Patent Number: 4,562,299

[45] Date of Patent: Dec. 31, 1985

[54] PROCESS FOR THE PREPARATION OF VICINAL DIOLS SOLUBLE IN WATER

[75] Inventors: Carlo Venturello; Mario Gambaro, both of Novara, Italy

[73] Assignee: Montedison S.p.A., Milan, Italy

[21] Appl. No.: 680,833

[22] Filed: Dec. 12, 1984

[30] Foreign Application Priority Data

Dec. 16, 1983 [IT] Italy .................... 24203 A/83

[51] Int. Cl.$^4$ ............... C07C 29/03; C07C 31/20; C07C 31/27; C07C 33/26
[52] U.S. Cl. .................. 568/811; 549/453; 568/658; 568/821; 568/833; 568/838; 568/847; 568/860
[58] Field of Search ........... 568/860, 811, 658, 821, 568/833, 838, 847; 549/453

[56] References Cited

U.S. PATENT DOCUMENTS

| | | | |
|---|---|---|---|
| 2,773,909 | 12/1956 | Smith | 568/860 |
| 2,833,787 | 5/1958 | Carlson et al. | 568/860 |
| 4,203,926 | 5/1980 | Wu et al. | 568/860 |
| 4,217,291 | 8/1980 | Wu et al. | 568/860 |
| 4,229,601 | 10/1980 | Wu et al. | 568/860 |
| 4,413,151 | 11/1983 | Michaelson et al. | 568/860 |

FOREIGN PATENT DOCUMENTS

| | | | |
|---|---|---|---|
| 598858 | 5/1960 | Canada | 568/860 |
| 121229 | 7/1983 | Japan | 568/838 |

Primary Examiner—J. E. Evans
Attorney, Agent, or Firm—Stevens, Davis, Miller & Mosher

[57] ABSTRACT

A process for the preparation of water-soluble vicinal diols by means of a direct catalytic hydroxylation of the corresponding olefines with $H_2O_2$. An olefine possibly carrying functional groups inert under the reaction conditions, and whose corresponding vicinal diol is soluble in water, is made to react, under vigorous stirring, with $H_2O_2$ at a temperature between 0° and 120° C. and at a pressure between 1 and 100 atmospheres, in a two-phase aqueous liquid/organic liquid system consisting or consisting essentially of an acid aqueous phase containing $H_2O_2$ and of an organic phase containing (1) said olefine; (2) possibly a solvent immiscible with the aqueous phase; and (3) a catalyst of the formula:

$$Q_3XW_4O_{24-2n}$$

wherein Q represents an onium $(RR_1R_2R_3M)^+$ cation, wherein M is chosen from among N, P, As and Sb, and R, $R_1$, $R_2$ and $R_3$, equal to or different from each other, represent hydrogen atoms or hydrocarbon groups having a total of from 20 to 70 carbon atoms; X is an atom of P or As; and n is an integer chosen from among 0, 1 and 2.

12 Claims, No Drawings

PROCESS FOR THE PREPARATION OF VICINAL DIOLS SOLUBLE IN WATER

DESCRIPTION

The present invention relates to a process for the preparation of vicinal diols soluble in water. More particularly, this invention relates to a process for the preparation of such diols by a direct catalytic hydroxylation of the corresponding olefins with hydrogen peroxide.

The water-soluble vicinal diols are products of particular interest for the chemical industry. They are prevailingly used as intermediates in the pharmaceutical industry, in photography, in the textile industry, the cosmetic industry, for herbicides, in polymers and in additives for plastic materials.

For instance, 1-phenyl-1,2-ethandiol is used for the production of 2-phenylethanol (essence of roses), and the diester of trans-1,2-cyclohexandiol with lauric acid is used as a plasticizer for polyvinyl chloride.

Various different processes are known for the direct hydroxylation of olefins with $H_2O_2$. Some of these processes are based on the use of organic peracids, such as peracetic acid or performic acid, in general prepared on the spot (in situ), starting from $H_2O_2$ and the corresponding acids.

Other processes are based on the use in catalytic quantities of metal oxides, such as $OsO_4$ or $H_2WO_4$.

None of these processes proves, however, free of drawbacks. Thus, in the case of the hydroxylation of olefins catalyzed by $OsO_4$, serious problems are met as far as the cost and the toxicity of the catalyst is concerned and for the necessity of operating with anhydrous $H_2O_2$ solutions; moreover, the yields are not always satisfactory.

The hydroxylation of olefins catalyzed by tungstic acid turns out to be fully satisfactory, on the practical level, only when one starts from water-soluble olefinic compounds, such as for instance, ally alcohol, maleic acid and fumaric acid. With almost all the other substrates, because of the necessity of operating in the presence of suitable solvents (such as acetic acid) capable of solubilizing both reactants, there arises the economically rather burdensome problem of the isolation and purification of the product from the reaction mixture.

The problem is complicated, in the case of acetic acid as a solvent, by the necessity of saponifying with NaOH the intermediate hydroxy acetate that has formed in the reaction medium. Still another limitation of the method consists in the moderate effectiveness of the catalyst in the monophasic aqueous-organic system when using not particularly active substrates.

The problem of the isolation of the vicinal diol, with all the operations involved in it, constitutes also the critical point of the process via organic peracids, which is the most widely used on an industrial scale. In fact, it is not possible to attain directly in this way the desired product with a sufficiently high degree of purity. Burdensome preliminary treatments of the reaction mixture are required, which tretments comprise:

(1) removing by distillation (together with the unreacted olefine) and/or neutralization with sodium hydroxide of considerable quantities of organic acid which must somehow be recovered;

(2) successive operations with a solvent of the diol from the resulting reaction residue and/or fractional distillation operations.

Thus, one object of the present invention is that of providing an economically convenient process for the preparation of water-soluble vicinal diols by direct hydroxylation of the corresponding olefins with $H_2O_2$, which allows one to obtain the diols directly with a high degree of purity, thus avoiding recourse to laborious treatments of the reaction mixture.

Another object of the present invention is that of providing a catalytic process that shall allow one, just because of its being catalytic, to avoid the use of organic reactants, such as acetic acid or formic acid, used in considerable quantities.

Still another object of this invention is that of providing a process that uses a catalyst of low cost.

A still further object is that of providing a process that will allow one to use diluted aqueous solutions of $H_2O_2$, thereby obtaining an advantage both from the point of view of economy as well as with regard to operational safety, in comparison to the prior art, according to which latter most times there is used very concentrated $H_2O_2$.

All the above objects, as well as additional objects, are achieved by the process of the present invention for the preparation of a water-soluble vicinal diol by means of the catalytic hydroxylation of the corresponding olefine with $H_2O_2$.

This process is characterized in that an olefine possibly carrying functional groups inert under reaction conditions and whose corresponding vicinal diol is soluble in water, is made to react under vigorous stirring with $H_2O_2$, at a temperature between 0° and 120° C. and at a pressure between 1 and 100 atmospheres, in a two-phase aqueous liquid/organic liquid system consisting or consisting essentially of an aqueous acid phase containing $H_2O_2$ and an organic phase containing:

(1) the above-mentioned olefine;
(2) possibly a solvent immiscible with the aqueous phase; and
(3) a catalyst of the formula $Q_3XW_4O_{24-2n}$ wherein:

Q represents an onium $(RR_1R_2R_3M)^+$ cation in which M is chosen from amongst N, P, As and Sb, and R, $R_1$, $R_2$ and $R_3$, either equal to or different from each other, represent hydrogen atoms or hydrocarbon groups having a total of from 20 to 70 carbon atoms;
X is an atom of P or As; and
n is an integer chosen from amongst 0, 1 and 2.

The hydroxylation reaction of the olefines according to the present invention may be represented by the following equation:

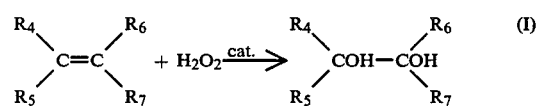

(I)

wherein:

$R_4$, $R_5$, $R_6$ and $R_7$, equal to or different from each other, are hydrogen atoms or hydrocarbon groups (such as alkyls, aryls or alkylaryls) possibly carrying functional groups inert under reaction conditions; the hydrocarbon groups and the possible functional groups being such as to ensure the solubility in water of the corresponding diols, and wherein, moreover, a hydrocarbon radical $R_4$ or $R_5$ attached to an ethylenic carbon, joining a hydrocarbon radical $R_6$ and $R_7$ attached to the other ethylenic carbon, may form an alkenylic cyclic group containing from 4 to 7 carbon atoms.

The functional groups inert under reaction conditions, equal to or different from each other, are for instance Cl, F, OH, $OCH_3$ and COOH. In general, there are from 0 to 3 such groups.

The catalysts $Q_3XW_4O_{24-2n}$ and the way to prepare them are described in European Patent Application No. 109,273.

These catalysts may be prepared as follows: first, there are made to react with each other tungstic acid or an alkali metal tungstate, phosphoric acid or an alkali metal phosphate (or a corresponding arsenic compound) and $H_2O_2$, contained in an acid aqueous phase. The reaction product thus obtained is then made to react with an onium salt contained in an organic solvent immiscible with water. The onium salt $Q^+Y^-$ consists of the already defined $Q^+$ cation and an inorganic $Y^-$ anion stable under reaction conditions, such as for example, $Cl^-$, $HSO_4^-$ or $NO_3^-$. The acid aqueous phase has preferably a pH below 2. In order to obtain such pH values, if necessary the pH is corrected with a mineral acid (for instance, $H_2SO_4$ or HCl).

The reaction between the above-indicated inorganic reactants in general is carried out at a temperature between 20° and 80° C.; thereupon there is added, preferably at room temperature, the onium salt in its solvent (for instance, dichloroethane or benzene); the stirring of the biphasic mixture is carried on for 15 to 20 minutes.

The molar ratio between the reactants are usually thus: for each gram atom of X (P or As), there are used 4 gram atoms of W and up to 2 mols of onium salt. As far as the $H_2O_2$ is concerned, it will be sufficient to use from 2.5 to 6 mols of $H_2O_2$ for each gram atom of W.

If the particular product that is formed turns out to be in the solid state, it will be directly separated from the biphasic mixture, for instance by filtering. In the contrary case, the organic phase will be separated, filtered and evaporated under vacuum at between 40° and 50° C., thereby obtaining the catalyst in the form of either a solid or a thick oil.

In the onium $(RR_1R_2R_3M)^+$ cation, M is chosen from amongst N, P, As and Sb. Preferably, there are used catalysts in which M is either N or P.

Radicals R, $R_1$, $R_2$ and $R_3$ have a total of from 20 to 70 carbon atoms. Preferably, there are used catalysts in which said total is between 25 and 40 carbon atoms.

There may also be used mixtures of $Q_3XW_4O_{24-2n}$ catalysts. The mixtures of such a type may be obtained, for instance, starting from commercial mixtures of onium salts, for example, from the one known by the commercial name of ARQUAD 2HT (dimethyl[dioctadecyl (75%)+dihexadecyl (25%)]ammonium chloride).

The hydroxylation reaction is conducted according to the double-phase technique. The organic phase contains the olefine, the catalyst and, possibly, a solvent immiscible with the aqueous phase. When no solvent is used, there will be used a suitable excess of olefine. The use or not of a solvent depends on the nature of the catalyst and of the olefine. In fact, the catalyst may sometimes be insoluble in the olefine. On the other hand, if the olefine is highly reactive, it may be convenient to use a solvent.

As solvents for the organic phase, there are used inert solvents immiscible with the aqueous phase. There may be used, for instance: (1) aromatic hydrocarbons, such as for example, benzene, toluene and the xylenes; (2) chlorinated hydrocarbons, such as for example, dichloromethane, trichloromethane, chloroethane, chloropropanes, dichloroethanes, trichloroethanes, tetrachloroethanes, dichloropropanes, trichloropropanes, tetrachloropropanes, chlorobenzene; and (3) alkyl esters, such as for example, ethyl acetate. There may also be used suitable mixtures of these solvents.

Olefinic compounds that may be conveniently used as starting substances are, for example, styrene, the various vinyltoluenes (ortho-, metha- para-), alpha-methylstyrene, cyclopentene, cyclohexene, cycloheptene, tetramethylethylene, 1-hexene, 1-pentene, 2-butene, propylene, allyl chloride, cinnamyl alcohol, isoeugenol, isosafrole, and beta-methylstyrene.

When one starts from cycloolefines, the cycloalkanediols have a trans-configuration.

The pH of the aqueous phase is habitually between 0 and 3, but preferably between 1 and 2. This aqueous phase may be acidified with mineral or organic acids, for example, sulphuric acid, phosphoric acid, and sulphonic acids; but preferably sulphuric acid is used.

The $H_2O_2$ concentration in the aqueous phase is usually between 1 and 10% by weight, but preferably is between about 2% and about 4%.

The operating temperature is determined by the reactivity and by the nature of the olefine, as well as by the stability of the hydrogen peroxide and of the catalyst used. In general, one operates at temperatures between 20° and 120° C., but more often at temperatures between about 40° and about 90° C.

The operating pressure is commonly atmospheric pressure. However, in the case of low-boiling olefins, it will be necessary to operate at a pressure sufficient (up to 100 atm) to maintain the olefine in the liquid state.

The reactants, that is the olefine and the $H_2O_2$, may be used in molar ratios corresponding substantially to the stoichiometry of the reaction. However, whether in the presence or in the absence of a suitable solvent, it will be advantageous to use an excess of olefine, in general corresponding to a molar ratio olefine/$H_2O_2$ between 1.5:1 and 5:1.

The catalyst is used in quantities in general between 0.005 and 0.1 gram atom of W per mol of $H_2O_2$, but preferably between about 0.01 and about 0.03 gram atom of W per mol of $H_2O_2$.

Whenever a solvent is used in the organic phase, the concentration of the olefine in the organic phase will generally be between 5% and 95% by weight, but preferably will be between about 40% and about 80% by weight.

The duration of the reaction depends on the nature and on the quantity of catalyst used and on the type of olefine used. In general, a time between 1 and 5 hours will be sufficient for completing the reaction.

At the end of the reaction, the vicinal diols that have formed may be directly recovered from the aqueous phase by using traditional techniques after the preliminary destruction, according to known methods, of the still present residual $H_2O_2$. One may, for example, operate as follows: the residual $H_2O_2$ is destroyed with, e.g., sodium metabisulphite; the aqueous phase is then neutralized and brought to dryness by evaporation under a reduced pressure; the diol is then extracted from the dry residue by means of a suitable solvent, for instance ether, acetone or ethyl acetate. In certain cases the diol will be partially present in the organic phase, wherefore it will be convenient to repeatedly extract that phase with water in order to complete the recovery of the desired diol.

The examples that follow are given in order to still more clearly illustrate this invention.

EXAMPLE 1

Into a 300 ml reactor fitted with a reflux coolant, a thermometer and a mechanical stirrer, there were introduced 30 ml of styrene (261 mmols), 1.70 g of catalyst

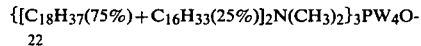

(equal to 2.5 mols of W), and an aqueous solution of $H_2O_2$ obtained by dissolving 8.5 ml of $H_2O_2$ in a 40% concentration by weight/volume (400 g/lt)) (100 mmols), in 160 ml of $H_2O$, and by bringing the pH value of the resulting solution to 1.5 with a 30% b.w. $H_2SO_4$.

The resulting biphasic mixture was quickly brought, under vigorous stirring, to 60° C. and then maintained at this temperature for 75 minutes. After cooling down, there were added 4 ml of a 30% b.w. $H_2SO_4$ in order to facilitate the separation of the phases. The aqueous phase was then separated and filtered on a paper filter and then additioned with sodium metabisulphite in order to destroy the $H_2O_2$ still present.

The solution was thereupon brought up to a pH of about 8 by the addition of solid $Na_2CO_3$, after which it was brought to dryness.

The solid residue was then extracted with ethyl ether (100 ml) and kept under stirring under reflux. This treatment was repeated three times.

Then, by evaporation of the ether solution, there were obtained 11.70 g of 1-phenyl-1,2-ethanediol as a white solid (gas chromatographic titer: 99%).

The yield in diol (expressed as diol at 100%) is equal to 84% (calculated on the $H_2O_2$ charged to the process).

By extraction of the organic phase with water acidified with $H_2SO_4$ there could be obtained a further quantity (0.20–0.25 g) of sufficiently pure diol.

EXAMPLE 2

Example 1 was repeated, except for using alpha-methylstyrene (34 ml; 260 mmols) instead of styrene. There were thus obtained 12.60 g of 2-phenyl-1,2-propandiol as a white solid (gas chromatographic titer 99%). The yield in diol (expressed as 100% diol) amounted to 82% (calculated on the $H_2O_2$ charged).

By treating the organic phase there could be obtained a further 0.4–0.5 g of sufficiently pure diol.

EXAMPLE 3

Into a 250 ml reactor fitted with a reflux coolant, a thermometer and a mechanical stirrer, there were introduced: 15.35 ml of cyclohexene (150 mmols), 10 ml of benzene, 0.85 g of the same catalyst as that used in Example 1 (equal to 1.25 mmols of W) and an aqueous solution of $H_2O_2$ obtained by dissolving 8.5 ml of $H_2O_2$ at 40% by weight/volume (100 mmols) in 80 ml of $H_2O$ and by then bringing the pH value of the resulting solution to 1.5 with a 30% b.w. $H_2SO_4$.

The resulting biphasic mixture was rapidly brought up to 70° C. under vigorous stirring, and was then kept at this temperature for 60 minutes.

The procedure was then as in Example 1, except that the solid residue was extracted with acetone (3×150 ml) at 50° C. instead of ether. There were thus obtained 10.85 g of trans-1,2-cyclohexanediol as a white solid (gas chromatographic titer: 99%).

The yield of diol (expressed as a 100% diol) was equal to 92% (calculated on the $H_2O_2$ charged).

EXAMPLE 4

Example 3 was repeated using the catalyst:

(0.695 g, equal to 1.25 mmols of W).

There were thus obtained 10.77 g of trans-1,2-cyclohexanediol as a white solid (gas chromatographic titer: 99%). The yield in diol (expressed as diol in a 100%) amounted to 92% (calculated on the $H_2O_2$ charged).

EXAMPLE 5

Example 3 was repeated, using cyclopentene (13.2 ml; 150 mmols) instead of cyclohexene, 1.365 g of the catalyst of Example 1 (equal to 2 mmols of W), and operating at 55° C. (bath temperature) for 2 hours. There were thus obtained 9.40 g of trans-1,2-cyclopentanediol in the form of a thick oil that solidified slowly (gas chromatographic titer: 98%).

The yield in diol (expressed as 100% diol) amounted to 90.3% (calculated on the $H_2O_2$ charged).

EXAMPLE 6

Examples 5 was repeated, but using cycloheptene (17.5 ml; 150 mmols) instead of cyclohexene and operating at 60° C. for 2 hours.

There were thus obtained 10.48 g of trans-1,2-cycloheptanediol as a white solid (gas chromatographic titer: 96%).

The yield in diol (expressed as 100% diol) was equal to 77.4% (calculated on the $H_2O_2$ charged).

By treatment of the organic phase there could be obtained further about 0.7 g of diol (gas chromatographic titer: 98.5%) which corresponded to a 5% yield.

EXAMPLE 7

Into a 300 ml reactor fitted with a reflux coolant, a thermometer and a mechanical stirrer, there were introduced 25 ml of 1-hexene (200 mmols), 1.67 g of the same catalyst used in Example 4 (equal to 3 mmols of W), 20 ml of 1,2-dichloroethane, and an aqueous solution of $H_2O_2$ obtained by dissolving in 150 ml of $H_2O$ 8.5 ml of a 40% w/v (100 mmols) of $H_2O_2$, and then bringing the pH of the resulting solution to 1 with a 30% by weight $H_2SO_4$.

The biphasic mixture thus resulting was then brought to reflux under vigorous stirring (temperature of the bath: 65° C.) and was then kept at this temperature for 3 hours. At the end there was added just a little ether (10–15 ml) in order to facilitate the separation of the phases.

The organic phase was thereupon extracted with $H_2O$ (4×70 ml). The aqueous extract was then combined with the aqueous phase. The resulting aqueous solution, after destruction of the residual $H_2O_2$, was brought up to a pH of about 8 with solid $Na_2CO_3$ and then brought to dryness. The residue was then extracted with acetone (3×150 ml).

By evaporation of the acetone solution there were obtained 7.92 g of 1,2-hexanediol in the form of an oil (gas chromatographic titer: 96%).

The yield in diol (expressed as 100% diol) amounted to 64% (calculated on the $H_2O_2$ charged).

EXAMPLE 8

Example 7 was repeated, but using allyl chloride (20.5 ml; 250 mmols) instead of 1-hexene, operating at 66°–68° C. (temperature of the bath) for 3½ hours. At the end of the operation, the aqueous phase was treated as in Example 7. The product obtained by evaporation of the acetone solution was eluted on a silica column with ether. By evaporation of the solvent there were obtained 7.87 g of 3-chloro-1,2-propanediol in the form of an oil (gas chromatographic titer: 98.7%).

The yield in diol (expressed as 100% diol) amounted to 70% (calculated on the $H_2O_2$ charged).

EXAMPLE 9

Into a 1 liter autoclave having a glass lining and fitted with a magnetic stirrer, there were introduced 3.34 g of the same catalyst used in Example 4 (equal to 6 mmols of W), 40 ml of 1,2-dichloroethane and an aqueous solution of $H_2O_2$ obtained by dissolving 17 ml of a 40% w/v $H_2O_2$ (200 mmols) in 160 ml of $H_2O$ and then bringing the pH of the resulting solution to 1 with 30% b.w. $H_2SO_4$.

After removing the air from the autoclave by applying a vacuum, there were loaded in said autoclave 42 g of propylene. The mixture was then heated up to 70° C. during about 1 hour under vigorous stirring, thereby attaining a pressure of 19 atmospheres. The reaction mixture was maintained at that temperature for 1 hour.

At the end of this operation, after cooling down (in about 1 hour) and after the removal of the gases, the autoclave was discharged. The aqueous phase was treated as in Example 7. There were thus obtained 8.80 g of 1,2-propanediol in the form of an oil (gas chromatographic titer: 97.4%).

The yield in diol (expressed as 100% diol) amounted to 56% (calculated on the $H_2O_2$ charged).

What is claimed is:

1. A process for the preparation of a water-soluble vicinal diol by means of the catalytic hydroxylation of the corresponding olefine with $H_2O_2$, characterized in that an olefine, possibly carrying functional groups inert under the reaction conditions and whose corresponding vicinal diol is soluble in water, is made to react, under vigorous stirring, with $H_2O_2$ at a temperature between 0° and 120° C., and at a pressure between 1 and 100 atmospheres, in a two-phase aqueous liquid/organic liquid system consisting essentially of an acid aqueous phase containing $H_2O_2$ and an organic phase containing:

(1) the above said olefine;
   (2) possibly a solvent immiscible with the aqueous phase; and
   (3) a catalyst of the formula $Q_3XW_4O_{24-2n}$ wherein
   Q represents an onium $(RR_1R_2R_3M)^+$ in which M is chosen from amongst N, P, As and Sb, and R, $R_1$, $R_2$ and $R_3$, equal to or different from each other, represent hydrogen atoms or hydrocarbon groups having a total of from 20 to 70 carbon atoms;
   X is an atom of P or As; and
   n is an integer chosen from among 0, 1 and 2.

2. A process according to claim 1, characterized in that in the onium $(RR_1R_2R_3M)^+$ cation, M is N or P.

3. A process according to claim 1 or 2, characterized in that in the onium $(RR_1R_2R_3M)^+$ cation, the radicals R, $R_1$, $R_2$ and $R_3$ have a total of from 25 to 40 carbon atoms.

4. A process according to claim 1 or 2, characterized in that the solvent immiscible with the aqueous phase is chosen from the group consisting of aromatic hydrocarbons, chlorinated hydrocarbons, and alkyl esters.

5. A process according to claim 1 or 2, characterized in that the pH of the aqueous phase is between 0 and 3.

6. A process according to claim 5, characterized in that the pH of the aqueous phase is between 1 and 2.

7. A process according to claim 1 or 2, characterized in that the concentration of $H_2O_2$ in the aqueous phase is between 1% and 10% by weight.

8. A process according to claim 1 or 2, characterized in that the temperature is between 20° and 120° C.

9. A process according to claim 8, characterized in that the temperature is between 40° and 90° C.

10. A process according to claim 1 or 2, characterized in that the molar ratio olefine/$H_2O_2$ is between 1.5:1 and 5:1.

11. A process according to claim 1 or 2, characterized in that the catalyst is used in a quantity between 0.005 and 0.1 gram atom of W per mol of $H_2O_2$.

12. A process according to claim 1 or 2, characterized in that the olefine is styrene or cyclohexene.

* * * * *